(12) United States Patent
Donaldson et al.

(10) Patent No.: US 8,491,512 B2
(45) Date of Patent: Jul. 23, 2013

(54) ADJUSTABLE CERVICAL COLLAR

(75) Inventors: Alan Donaldson, Lewisville, NC (US); Robert J. Weatherwax, Mooresville, NC (US)

(73) Assignee: Clear Advantage Collar, Inc., Charlotte, NC (US)

( * ) Notice: Subject to any disclaimer, the term of this patent is extended or adjusted under 35 U.S.C. 154(b) by 207 days.

(21) Appl. No.: 12/924,444

(22) Filed: Sep. 28, 2010

(65) Prior Publication Data
US 2012/0053499 A1    Mar. 1, 2012

Related U.S. Application Data

(60) Provisional application No. 61/402,237, filed on Aug. 26, 2010.

(51) Int. Cl.
*A61F 5/00* (2006.01)
(52) U.S. Cl.
USPC ........................................ 602/18; 128/DIG. 23
(58) Field of Classification Search
USPC ................................ 602/17–18; 128/DIG. 23
See application file for complete search history.

(56) References Cited

U.S. PATENT DOCUMENTS

| | | |
|---|---|---|
| 3,512,523 A | 5/1970 | Barnett |
| 3,916,885 A | 11/1975 | Gaylord, Jr. |
| 4,413,619 A | 11/1983 | Garth |
| 4,582,051 A | 4/1986 | Greene et al. |
| 4,987,891 A | 1/1991 | Gaylord, Jr. et al. |
| 5,058,572 A | 10/1991 | Schmid et al. |
| 5,060,637 A | 10/1991 | Schmid et al. |
| 5,215,517 A | 6/1993 | Stevenson et al. |
| 5,230,698 A | 7/1993 | Garth |
| 5,366,438 A | 11/1994 | Martin, Sr. |
| D359,584 S | 6/1995 | Wickert |
| D368,527 S | 4/1996 | Brooke |
| 5,520,619 A | 5/1996 | Martin |
| 5,588,957 A | 12/1996 | Martin, Sr. |
| 5,593,382 A | 1/1997 | Rudy, Jr. et al. |
| 5,622,529 A | 4/1997 | Calabrese |
| D379,232 S | 5/1997 | Brooke |
| 5,632,722 A | 5/1997 | Tweardy et al. |
| 5,688,229 A | 11/1997 | Bauer |
| 5,728,054 A | 3/1998 | Martin |
| D393,718 S | 4/1998 | Traut et al. |
| 5,795,315 A | 8/1998 | Traut et al. |
| 5,797,863 A | 8/1998 | Kohnke |
| 5,865,773 A | 2/1999 | Koledin |
| 5,993,403 A | 11/1999 | Martin |
| 6,036,664 A | 3/2000 | Martin, Sr. et al. |
| 6,045,523 A | 4/2000 | Donaldson |
| 6,056,711 A | 5/2000 | Domanski et al. |
| RE36,745 E | 6/2000 | Rudy, Jr. et al. |
| 6,071,255 A | 6/2000 | Calabrese |
| 6,090,058 A | 7/2000 | Traut et al. |

(Continued)

*Primary Examiner* — Patricia Bianco
*Assistant Examiner* — Camtu Nguyen
(74) *Attorney, Agent, or Firm* — Schwartz Law Firm, P.C.

(57) ABSTRACT

An adjustable cervical collar comprises an orthopedic brace assembly adapted for extending around a neck of a wearer, and an adjustable chin support adjacent the brace assembly. An infinitely variable actuator operatively interconnects the brace assembly and the chin support, and defines a infinitely variable linear displacement range between maximum and minimum limits of travel. A locking mechanism cooperates with the actuator to releasably lock the chin support in a selected position within the displacement range, thereby custom setting a height of the chin support relative to the brace assembly.

15 Claims, 12 Drawing Sheets

U.S. PATENT DOCUMENTS

| | | |
|---|---|---|
| 6,245,033 B1 | 6/2001 | Martin |
| 6,254,560 B1 | 7/2001 | Tweardy et al. |
| 6,423,020 B1 | 7/2002 | Koledin |
| 6,494,854 B1 | 12/2002 | Visness et al. |
| D479,878 S | 9/2003 | Phillips et al. |
| 6,663,581 B1 | 12/2003 | Calabrese |
| 6,726,643 B1 | 4/2004 | Martin |
| 6,872,188 B2 | 3/2005 | Caille et al. |
| 6,964,644 B1 | 11/2005 | Garth |
| 7,041,073 B1 | 5/2006 | Patron |
| 7,090,652 B2 | 8/2006 | Santelli, Jr. |
| 7,128,724 B2 | 10/2006 | Marsh |
| 7,141,031 B2 | 11/2006 | Garth et al. |
| 7,399,288 B2 | 7/2008 | Chao |
| 7,449,005 B2 | 11/2008 | Pickering et al. |
| 7,470,243 B2 | 12/2008 | Garth |
| 7,549,970 B2 | 6/2009 | Tweardy |
| 7,674,234 B2 | 3/2010 | Calco et al. |
| 2004/0204666 A1* | 10/2004 | Marsh ............................ 602/18 |
| 2008/0156332 A1* | 7/2008 | Ray ............................... 128/845 |

* cited by examiner

ADJUSTABLE CERVICAL COLLAR

TECHNICAL FIELD AND BACKGROUND

The present disclosure relates broadly and generally to cervical collars. In one exemplary embodiment, the present cervical collar incorporates an infinitely variable adjustment mechanism designed for custom fitting the collar to a wide range of users.

SUMMARY OF EXEMPLARY EMBODIMENTS

Various exemplary embodiments of the present invention are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises an adjustable cervical collar. The collar comprises an orthopedic brace assembly adapted for extending around a neck of a wearer, and an adjustable chin support adjacent the brace assembly. An infinitely variable actuator operatively interconnects the brace assembly and the chin support, and defines an infinitely variable displacement range between maximum and minimum limits of travel. The adjustable chin support is movable to any desired point along the displacement range defined by the actuator. A locking mechanism cooperates with the infinitely variable actuator to releasably lock the chin support in a selected position, thereby custom setting a height of the chin support relative to the brace assembly.

The term "infinitely variable" is defined herein to mean freely changeable beyond a pre-determined or pre-measured quantity or value. In an exemplary embodiment, the height of the chin support relative to the orthopedic brace assembly is "infinitely variable" between maximum and minimum limits of travel, such that the chin support can be adjusted vertically (e.g. by sliding one element relative to another) and locked into the desired position.

According to another exemplary embodiment, the brace assembly comprises a longitudinally flexible wrap-around neck shell.

According to another exemplary embodiment, the brace assembly further comprises a longitudinally flexible wrap-around neck cushion attached to the neck shell.

According to another exemplary embodiment, the chin support comprises a central bridge forming a substantially flat chin platform, and opposing wing panels integrally formed with the bridge.

According to another exemplary embodiment, the chin support further comprises a chin cushion mounted on the central bridge between the opposing wing panels. In the exemplary embodiment, the chin cushion and chin support comprise an integrally-formed, unitary, combination cushion/support for a mandible region of the wearer.

According to another exemplary embodiment, the infinitely variable actuator comprises a toothed rack integrally-formed with at least one of the wing panels of the chin support, and a rotatable toothed pinion gear operatively engaging the rack. The pinion gear cooperates with the rack to enable infinitely variable (linear) displacement of the chin support relative to the brace assembly.

According to another exemplary embodiment, the locking mechanism comprises a slide lock having at least one locking tooth adapted for selectively engaging the pinion gear in a gear-locked position to prevent rotation of the pinion gear and displacement of the chin support. The slide lock is movable from the gear-locked position to a gear-released position allowing free rotation of the pinion gear.

According to another exemplary embodiment, the slide lock further comprises a retention insert adapted to snap-fit within a shaped opening formed with the brace assembly, thereby retaining the slide lock in the gear-locked position.

According to another exemplary embodiment, the brace assembly and adjustable chin support are constructed of a substantially transparent material.

According to another exemplary embodiment, a numerical height indicator displays a selected height level of the adjustable chin support relative to the brace assembly. The height indicators on both wing panels may serve to vertically align both sides of the adjustable chin support in substantial registration. For example, precise vertical alignment may occur when both indicators display the same number.

In yet another exemplary embodiment, the present disclosure comprises a cervical collar comprising an orthopedic brace assembly and adjustable chin support. The brace assembly is adapted for extending around a neck of wearer. The adjustable chin support resides adjacent the brace assembly, and comprises a toothed gear rack. The gear rack defines a linear displacement range between maximum and minimum limits of travel. A rotatable toothed pinion gear operatively engages the gear rack, and cooperates with the gear rack to control travel of the chin support within the displacement range defined by the gear rack. A locking mechanism is adapted for selectively engaging the toothed pinion gear to releasably lock the chin support in a selected position, thereby custom setting a height of the chin support relative to the brace assembly.

In yet another exemplary embodiment, the present disclosure comprises a method using an adjustable cervical collar for adjustably supporting a chin of a wearer. The method includes applying an orthopedic brace assembly of the cervical collar to a neck of the wearer. A chin support of the cervical collar is slid vertically between maximum and minimum limits of travel. At any infinitely variable point between the maximum and minimum limits of travel, the chin support is releasably locked in a desired fixed position relative to the brace assembly.

The exemplary cervical collar incorporates design features shown in the attached drawings which enable substantially infinite vertical adjustment of the combined chin cushion/support. The unique rack-and-pinion type linear actuator allows providers to carry a limited number of emergency extrication cervical collars with the ability to have the correctly fitting collar for any size patient. It is also conceivable to have this infinitely adjustable feature incorporated into the circumferential sizing as well as the vertical height sizing requirements.

BRIEF DESCRIPTION OF THE DRAWINGS

The description of exemplary embodiments proceeds in conjunction with the following drawings, in which.

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
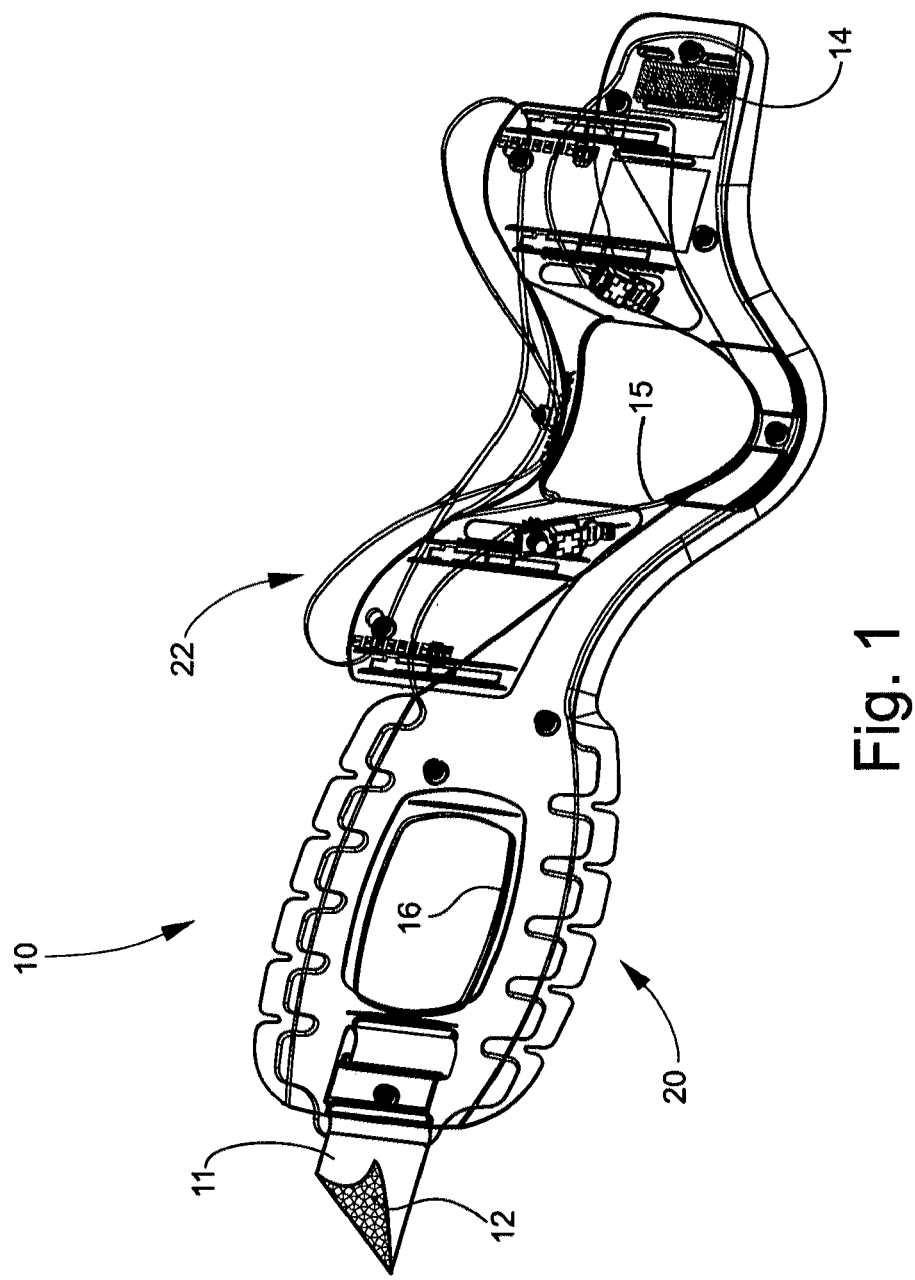
FIG. 1 is a perspective view of an adjustable cervical collar according to one exemplary embodiment of the present disclosure, and showing the cervical collar in a normally opened (or substantially flat) condition.
Figure 2:
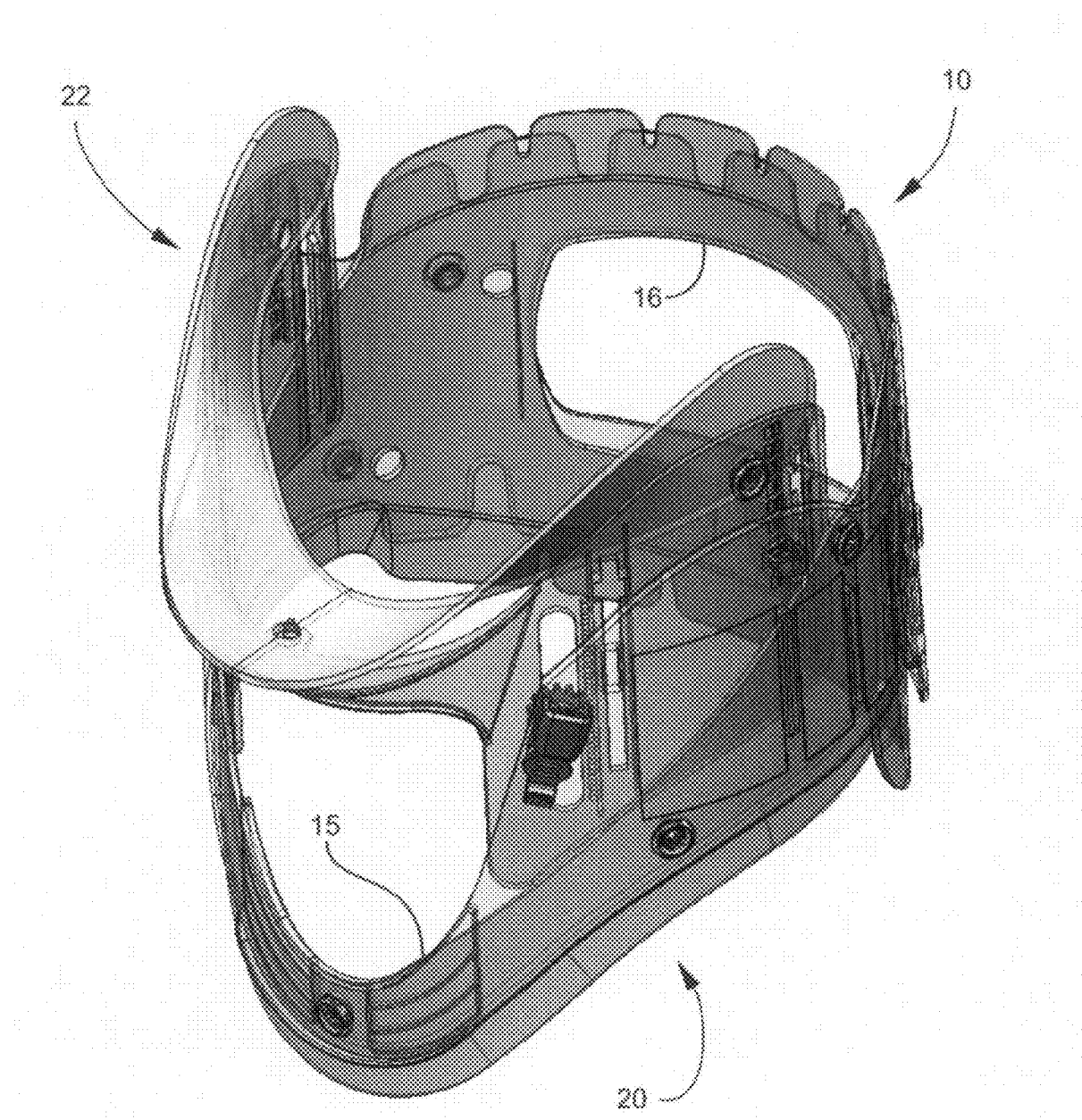
FIG. 2 is a perspective view of the adjustable cervical collar in a closed (as-used) condition as wrapped around the neck of a wear.
Figure 3:
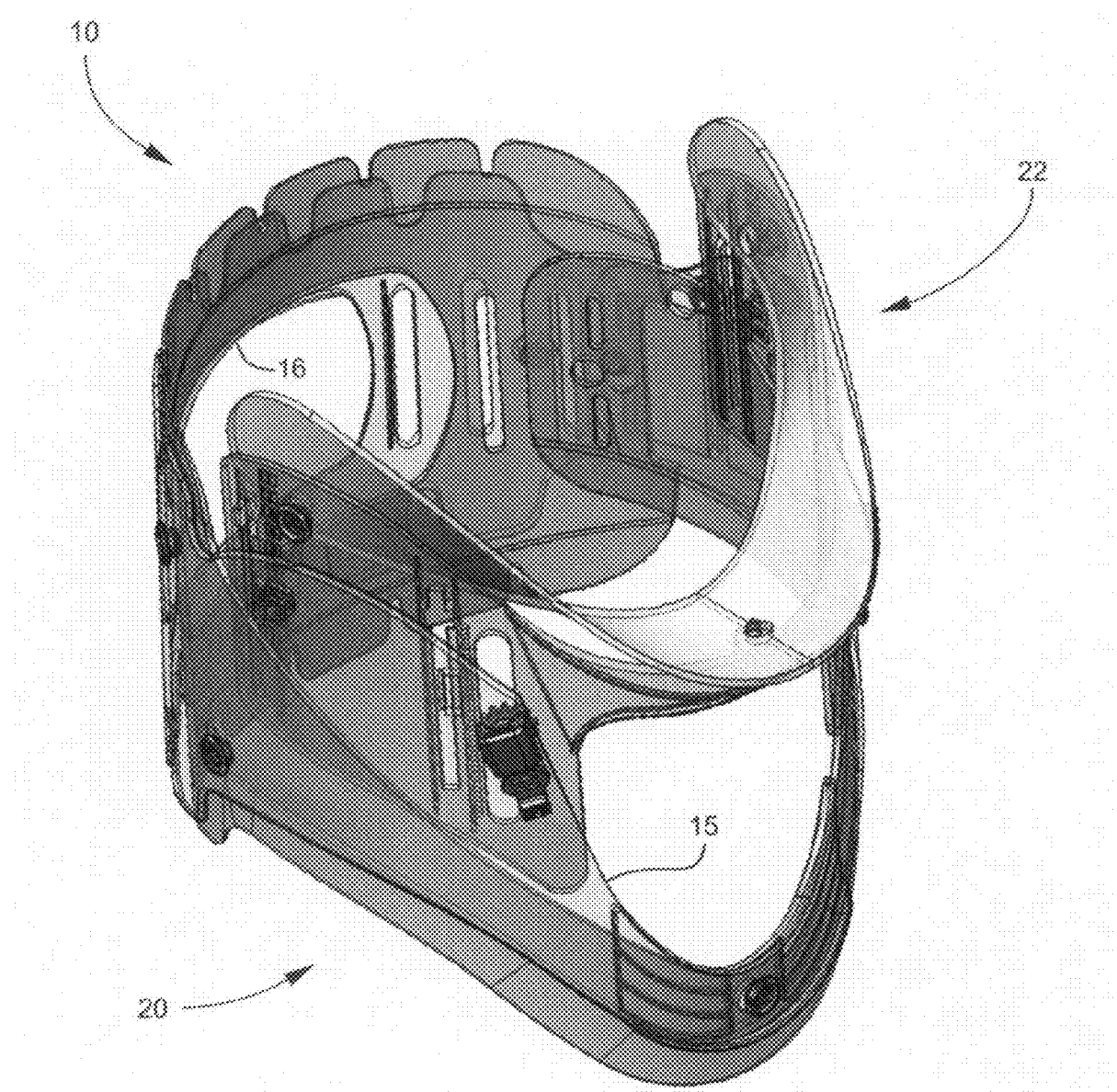
FIG. 3 is a second perspective view of the adjustable cervical collar in the closed condition.

Referring now specifically to the drawings, an adjustable multi-piece cervical collar according to one exemplary embodiment of the present invention is illustrated in FIG. 1, and shown generally at reference numeral 10. The exemplary cervical collar 10 is designed to wrap around the neck of a wearer in a closed condition, shown in FIGS. 2 and 3, to support the head and cervical portion of the spinal cord. In the embodiment shown, a flexible strap 11 with loop fasteners 12 (FIG. 1) mates with complementary hook fasteners 14 at an opposite end of the cervical collar 10 to adjustably fit the collar to the wearer. The present cervical collar 10 may be used by emergency medical services personnel for victims of traumatic head or neck injuries, to treat chronic medical conditions, and for strains, sprains or whiplash. The cervical collar 10 may also be therapeutic—helping to realign a wear's spinal cord and relieve pain. The cervical collar 10 may be used alone or in combination with other medical equipment, such as a halo commonly worn during recovery after surgeries. In other applications, the cervical collar 10 may be used as a protective brace to avoid whiplash and other neck injuries in high-risk activities and other non-medical uses, such as motorsports (e.g., Motorcross), go-kart racing, and speed-boat racing.

When positioned on a wearer, the present cervical collar 10 may define anterior and posterior windows 15, 16 designed to allow continuous access to areas of the neck, while substantially the entire neck may be visually monitored through clear structural components of the collar 10. In the event the wearer requires an emergency medical procedure, such as a tracheotomy or cricothyrotomy, that procedure can be undertaken through the anterior window 15, as is conventional in cervical collars. In the present cervical collar 10, the medical professional may be aided by the fact that the neck and the operating equipment and medical professional's hands can be seen through the collar 10 and not merely through the windows 15, 16. This and other advantages of substantially transparent (or "clear") cervical collars are discussed further in prior U.S. Pat. No. 6,045,523 issued to a co-inventor of the present application; the entire disclosure of this prior patent being incorporated by reference herein.

Figure 4:
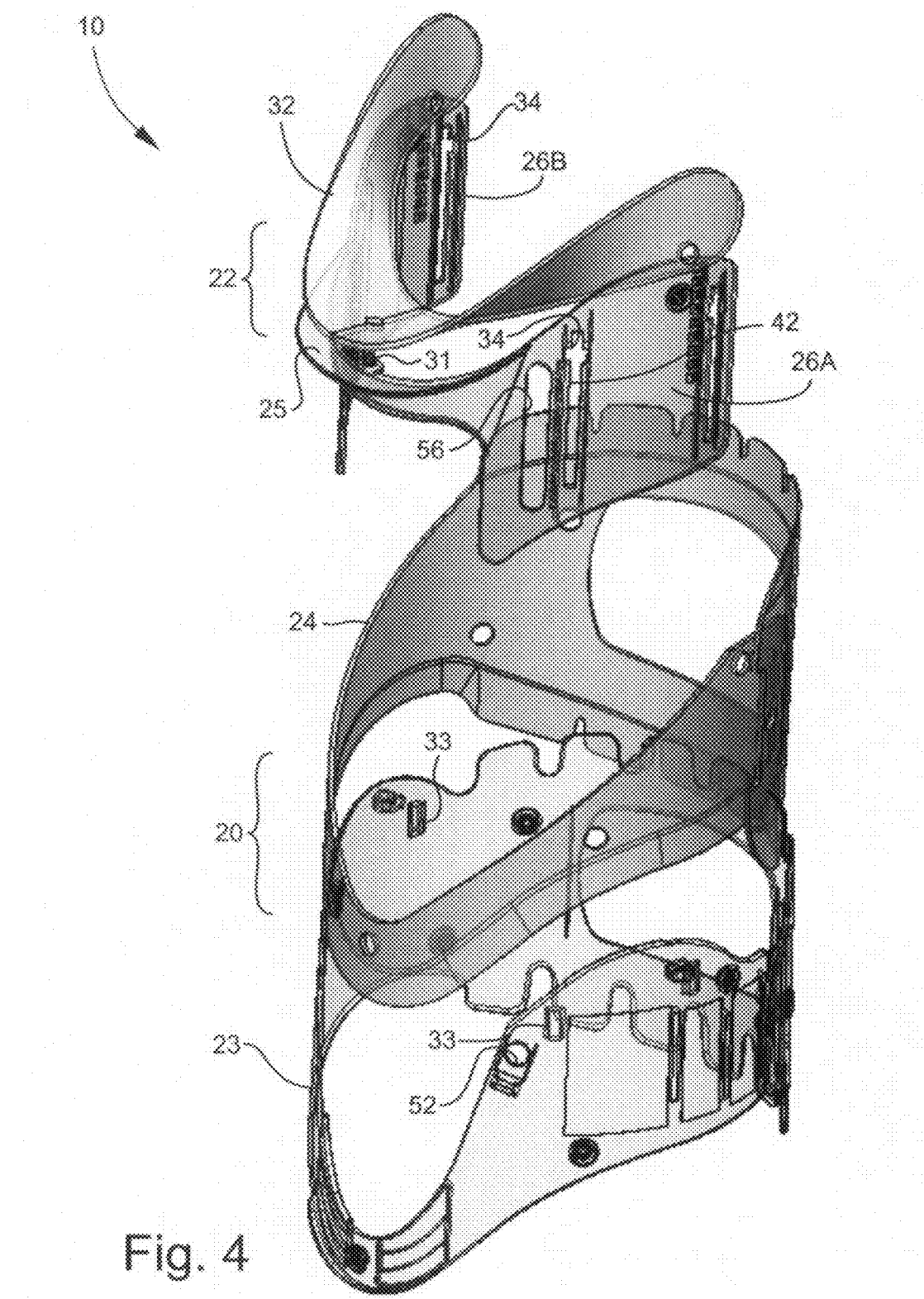
FIG. 4 is a perspective view of the cervical collar in the closed condition with various component parts exploded away.
Figure 5:
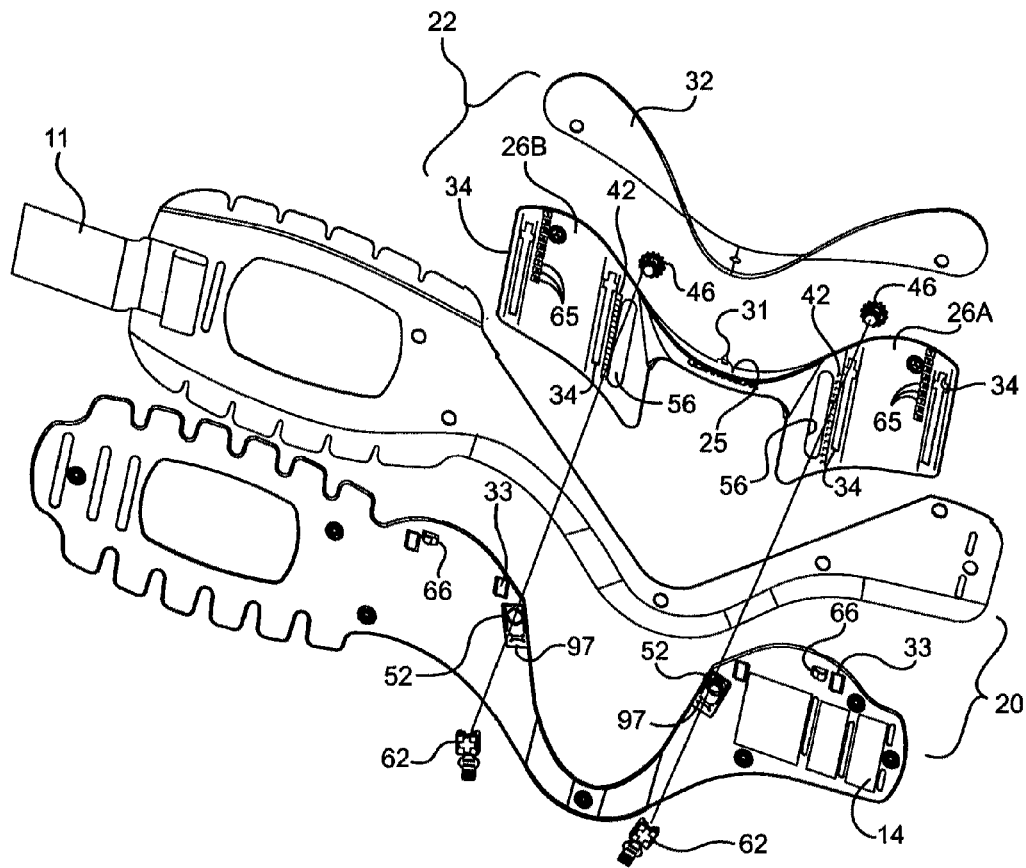
FIG. 5 is a perspective view of the cervical collar in the opened condition with various component parts exploded away.

Referring to FIGS. 4 and 5, the exemplary cervical collar 10 incorporates an orthopedic two-piece brace assembly 20 and custom adjustable chin support 22. The brace assembly 20 comprises a laterally (or vertically) stiff and longitudinally flexible, wrap-around neck shell 23, and corresponding wrap-around neck cushion 24. The exemplary neck shell 23 is formed of a substantially transparent, semi-rigid thermoplastic material. Other suitable materials may include acrylic, lexan, polycarbonate, clear cellulose propionate, PETG polyester, clear PVC, amorphous polystyrene, cross-linked polystyrene derivatives, and amorphous polyethylene terephthalate (aPET), as well as others. The exemplary neck cushion 24 is formed of a substantially transparent soft rubber or other cushioning material, and may be permanently or releasably attached to an inside of the neck shell 23 via spaced rivets, complementary fasteners, snaps, or other means.

The adjustable chin support 22 comprises a rigid central bridge 25 and opposing integrally-formed symmetrical wing panels 26A, 26B. The two wing panels 26A, 26B have identical features and structure, and cooperate with corresponding (identical) elements discussed below in effecting linear vertical adjustment of the chin support 22. The central bridge 25 and wing panels 26A, 26B may be constructed of a substantially transparent material, such as that described above with reference to the neck shell 23. The central bridge 25 forms a generally flat outward-projecting platform for the chin of the wearer, and has a vertical mounting post 31 for locating a chin cushion 32 fixedly attached to the opposing wing panels 26A, 26B by rivets. The exemplary chin cushion 32 may be constructed of a substantially transparent soft rubber material, and is positioned to reside generally adjacent the lower jaw (or mandible) of the wearer. The adjustable chin support 22 is slidably attached to the brace assembly 20 by cooperating T-shaped retainers 33 integrally formed with the neck shell 23, and received within respective vertical slots 34 defined by the wing panels 26A, 26B.

Figure 6:
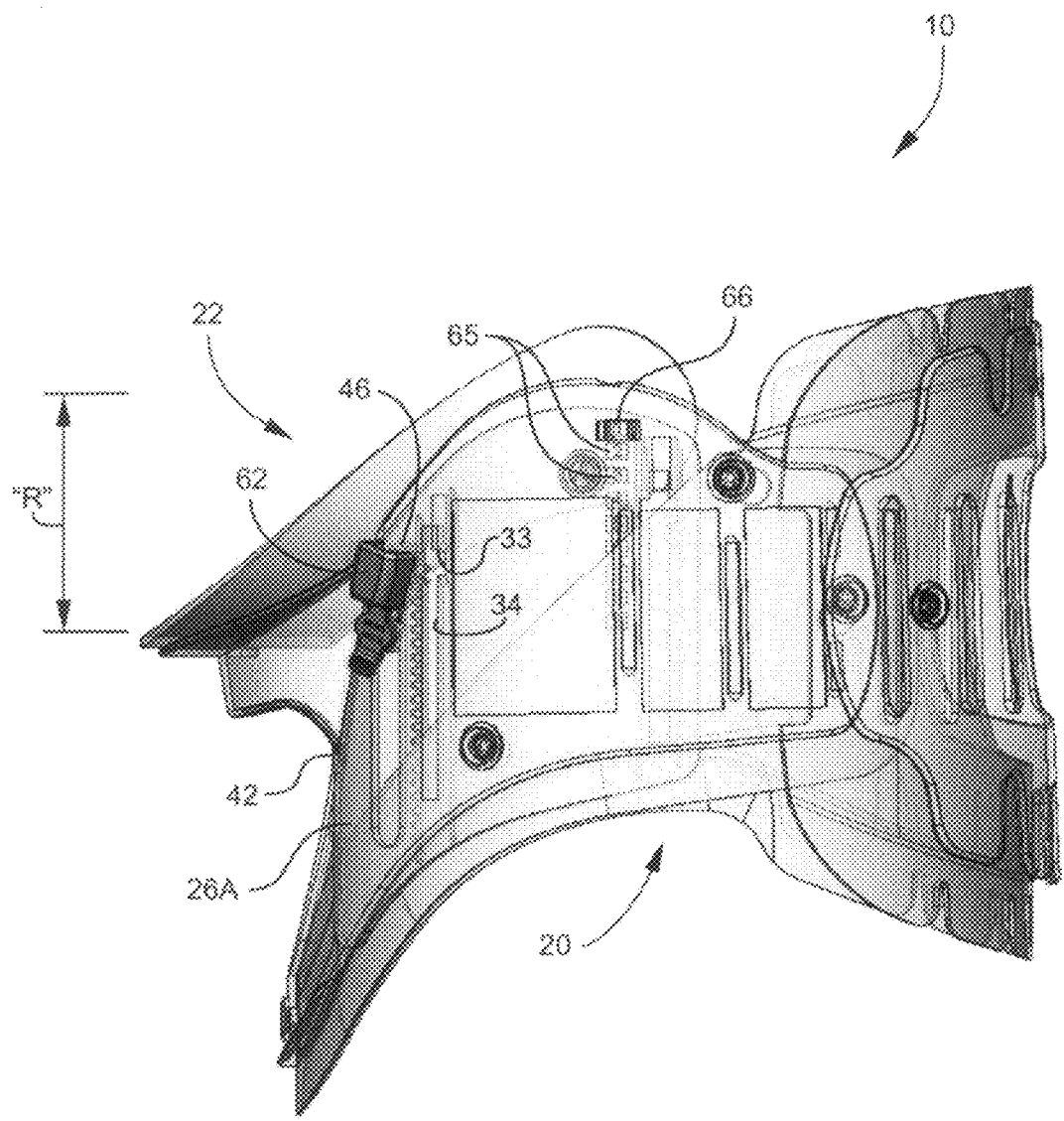
FIG. 6 is a side elevation of the cervical collar in the closed condition, and showing the adjustable chin support at a minimum height relative to the brace assembly.
Figure 7:
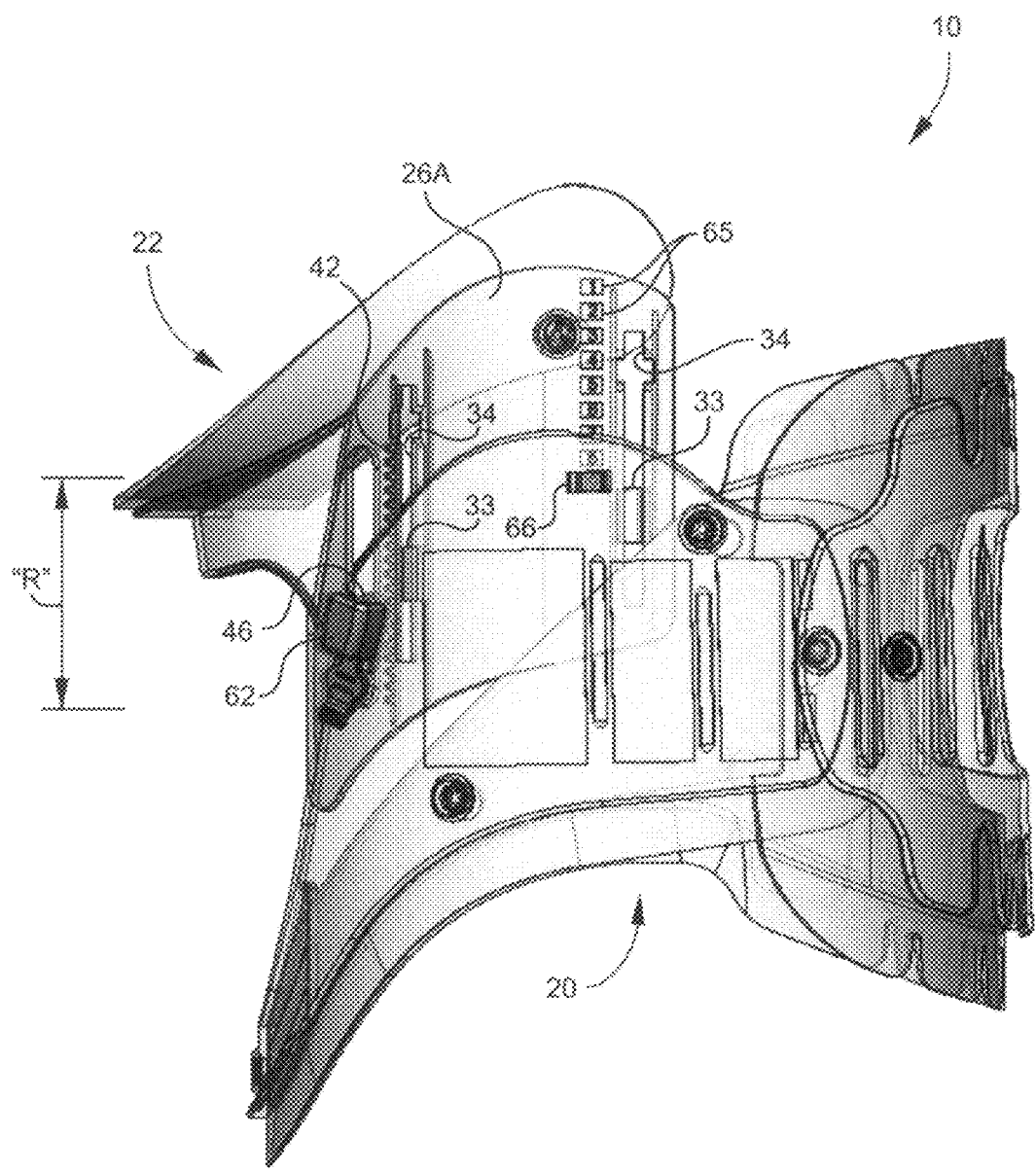
FIG. 7 is a side elevation of the cervical collar in the closed condition, and showing the adjustable chin support at a maximum height relative to the brace assembly.

Referring to FIGS. 5, 6, and 7, the adjustable chin support 22 with combined chin cushion 32 is operatively interconnected to the brace assembly 20 by an infinitely variable actuator comprising corresponding linear racks 42 formed with respective wing panels 26A, 26B and corresponding rotatable pinion gears 46. The pinion gears 46 insert through respective gear holes 52 in the outer neck shell 23, and through respective corresponding vertical displacement slots 56 formed with the wing panels 26A, 26B of the adjustable chin support 22. The displacement slots 56 define an infinitely variable range of vertical adjustment of the chin support 22 between maximum and minimum limits of travel. For example, FIGS. 6 and 7 show the adjustable chin support 22 at minimum and maximum heights, respectively, relative to the brace assembly 20. When the chin support 22 is moved vertically, the intermeshing teeth of pinion gears 46 and racks 42 cause the pinion gears 46 to rotate clockwise and counter-clockwise as the adjustable chin support 22 is raised and lowered within the displacement range "R". The chin support 22 is freely (e.g., manually) slidably adjustable between the minimum and maximum heights shown, and can be releasably locked at any desired (infinitely variable) point therebetween by corresponding slide locks 62 described below. The T-shaped retainers 33 received within respective vertical slots 34 of wing panels 26A, 26B hold the adjustable chin support 22 closely adjacent to the brace assembly 20 during adjustment and wear. The adjusted height of the chin support 22 can be measured (e.g., for alignment purposes) using numbered settings 65 located on each wing panel 26A, 26B, and designed to display through a settings window 66 formed with the outer neck shell 23.

Figure 8:
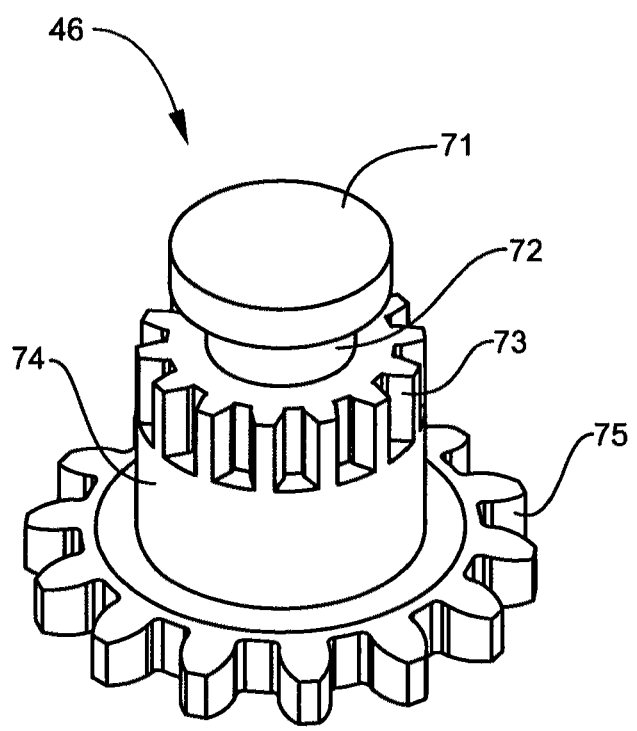
FIG. 8 is a perspective view of an exemplary pinion gear incorporated in the present infinitely variable rack-and-pinion actuator.
Figure 9:
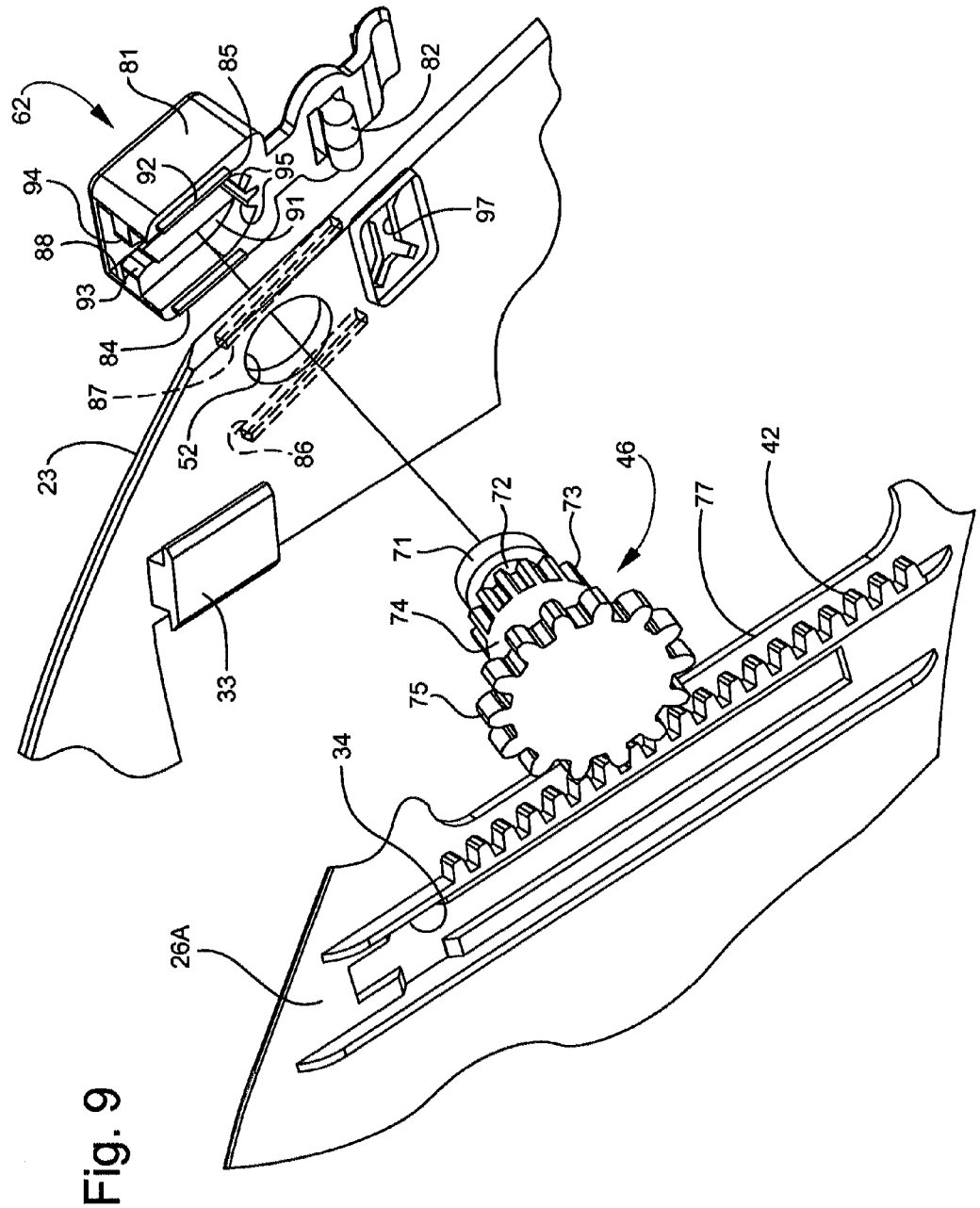
FIG. 9 is an exploded fragmentary view illustrating various component parts of the rack-and-pinion actuator.
Figure 10:
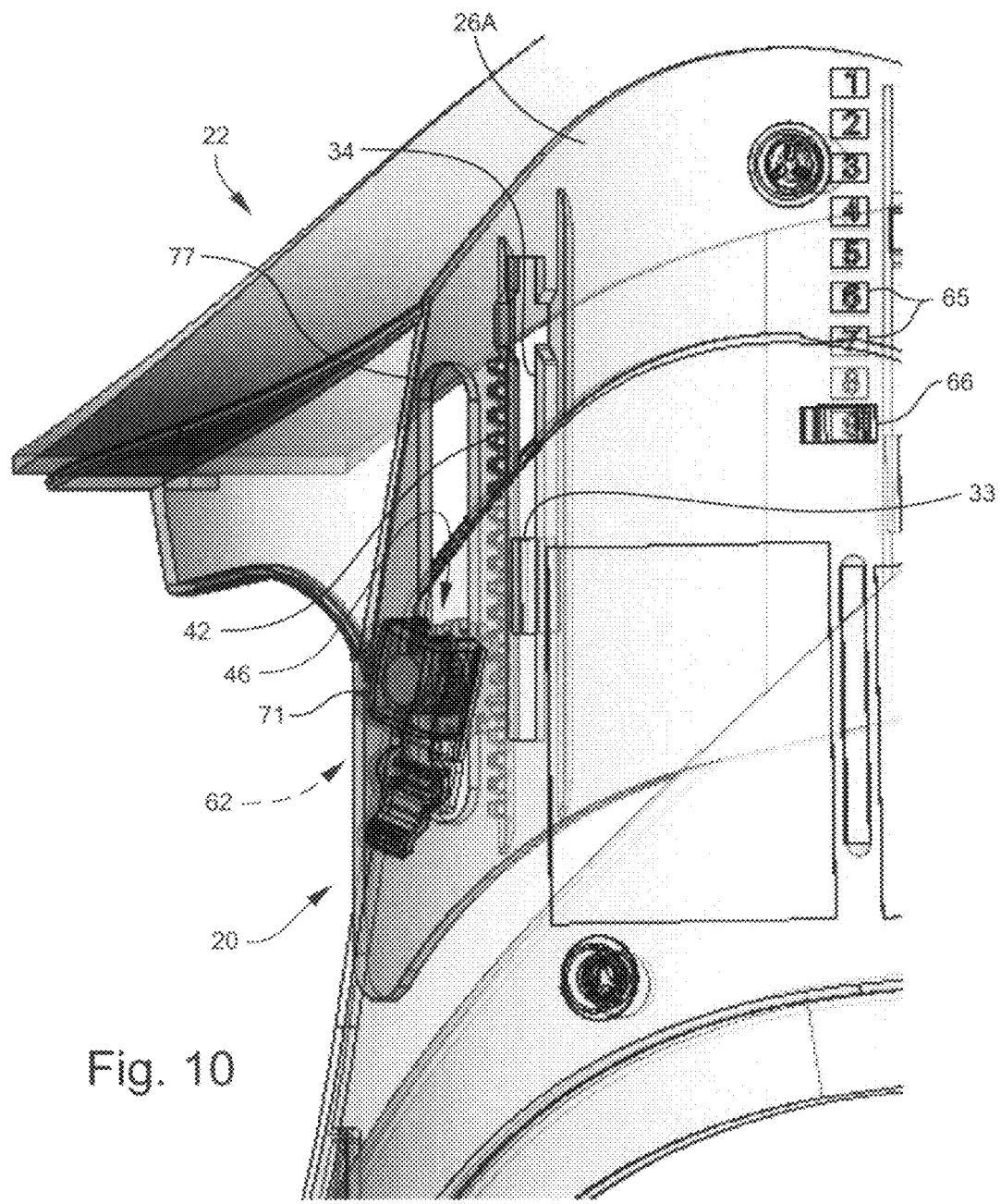
FIG. 10 is an enlarged fragmentary view of the exemplary cervical collar showing the rack-and-pinion actuator and releasable pinion slide lock.

As best shown in FIGS. 8, 9, and 10, each pinion gear 46 has an annular head 71, reduced-diameter neck 72, an intermediate-diameter toothed locking wheel 73, a cylindrical wheel spacer 74, and an enlarged-diameter toothed gear wheel 75. The pinion gear 46 is located at the displacement slot 56 of the wing panel 26A, as shown in FIGS. 9 and 10, such that the gear wheel 75 resides immediately adjacent an inside marginal slot edge 77 in teeth-meshing alignment with the linear rack 42, while the spaced locking wheel 73 resides outside of gear hole 52 immediately adjacent the outer neck shell 23 of the brace assembly 20. The annular head 71 of the pinion gear 46 projects outwardly from the locking wheel 73 and brace assembly 20, as shown in FIG. 10.

Figure 11:
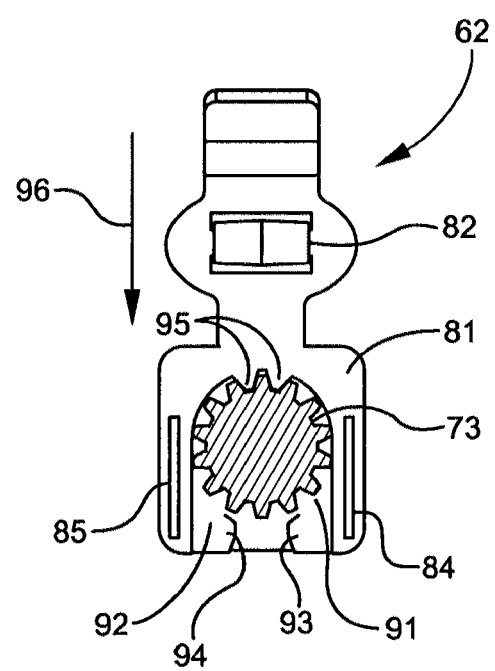
FIGS. 11 and 12 are views demonstrating operation of the pinion slide lock.
Figure 12:
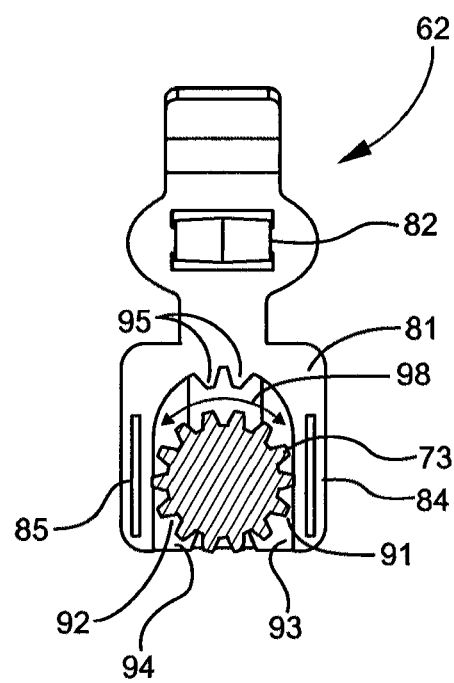

Referring to FIGS. 9, 11, and 12, each slide lock 62 incorporates an integrally formed hollow pinion block 81 and hinged retention insert 82 which function as a "brake" to restrict rotation of the pinion gear 46, thereby locking the adjustable chin support 22 in a fixed vertical position relative to the brace assembly 20. As best shown in FIG. 9, the pinion block 81 is mounted to the base assembly 20 via opposing rails 84, 85 which are slidably received within respective grooves 86, 87 formed with the outer neck shell 23. The pinion block 81 comprises an internal track 88 which receives the annular head 71 of the pinion gear 46 along spaced shoulders 91, 92, and inwardly-projecting stops 93, 94 which prevent the slide lock 62 from separating from the pinion gear 46. One or more locking teeth 95 are integrally formed with an inside rear of the pinion block 81, and function to engage the teeth of the pinion gear locking wheel 73 when the slide lock 62 is moved forward as indicated by arrow 96 into a gear-locked position. In this position, the hinged retention insert 82 of the slide lock 62 may be snap-fit into a shaped opening 97 formed with the outside neck shell 23 such that the block teeth 95 remain in locking engagement with teeth of the pinion gear locking wheel 73, thereby restricting rotation of pinion gear 46 and vertical adjustment of the chin support 22. To release the slide lock 62, the wearer removes the retention insert 82 from shell opening 97, and slides the pinion block 81 rearwardly to disengage block teeth 95 from teeth of the pinion gear locking wheel 73. In this position, the pinion gear 46 is freely rotatable as indicated by arrow 98, and the chin support 22 free to move vertically to any infinitely variable height within the displacement range "R" defined by wing slots 56, 58. After selecting the desired support height, the wearer can engage the slide locks 62, 64 as discussed above thereby fixing the height of the chin support 22 relative to the base assembly 20.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under §112, 6th paragraph is not intended. Additionally, it is not intended that the scope of patent protection afforded the present invention be defined by reading into any claim a limitation found herein that does not explicitly appear in the claim itself.

What is claimed:

1. An adjustable cervical collar, comprising:
   an orthopedic brace assembly adapted for extending around a neck of a wearer;
   an adjustable chin support adjacent said brace assembly, said chin support comprising a central bridge, and opposing wing panels integrally formed with the bridge;
   an infinitely variable actuator operatively interconnecting said brace assembly and said chin support, and defining an infinitely variable displacement range between maximum and minimum limits of travel, wherein said infinitely variable actuator comprises a toothed rack integrally-formed with at least one of the wing panels of said chin support, and a rotatable toothed pinion gear operatively engaging said rack; and
   a locking mechanism cooperating with said infinitely variable actuator to releasably lock said chin support in a selected position within the displacement range, thereby custom setting a height of said chin support relative to said brace assembly, wherein said locking mechanism comprises a slide lock having at least one locking tooth adapted for selectively engaging said pinion gear in a gear-locked position to prevent rotation of said pinion gear and displacement of said chin support, and said slide lock being movable from the gear-locked position to a gear-released position allowing free rotation of said pinion gear.

2. An adjustable cervical collar according to claim 1, wherein said brace assembly comprises a longitudinally flexible wrap-around neck shell.

3. An adjustable cervical collar according to claim 2, wherein said brace assembly further comprises longitudinally flexible wrap-around neck cushion attached to said neck shell.

4. An adjustable cervical collar according to claim 1, wherein said slide lock further comprises a retention insert adapted to snap-fit within a shaped opening formed with said brace assembly, thereby retaining said slide lock in the gear-locked position.

5. An adjustable cervical collar according to claim 1, wherein said chin support further comprises a chin cushion mounted on the central bridge between the opposing wing panels.

6. An adjustable cervical collar according to claim 1, wherein said brace assembly and adjustable chin support are constructed of a substantially transparent material.

7. An adjustable cervical collar according to claim 1, and comprising a numerical height indicator displaying a selected height level of said adjustable chin support relative to said brace assembly.

8. An adjustable cervical collar, comprising:
   an orthopedic brace assembly adapted for extending around a neck of wearer;
   an adjustable chin support adjacent said brace assembly and comprising a toothed gear rack, said gear rack defining a linear displacement range between maximum and minimum limits of travel;
   a rotatable toothed pinion gear operatively engaging said gear rack, and cooperating with said gear rack to control travel of said chin support within the displacement range defined by said gear rack; and
   a locking mechanism to releasably lock said chin support in a selected position, thereby custom setting a height of said chin support relative to said brace assembly, wherein said locking mechanism comprises a slide lock having at least one locking tooth adapted for selectively engaging said pinion gear in a gear-locked position to prevent rotation of said pinion gear and displacement of said chin support, and said slide lock being movable from the gear-locked position to a gear-released position allowing free rotation of said pinion gear.

9. An adjustable cervical collar according to claim 8, wherein said chin support comprises a central bridge and opposing wing panels integrally formed with said bridge.

10. An adjustable cervical collar according to claim 9, wherein said gear rack is integrally-formed with at least one of the wing panels of said chin support.

11. An adjustable cervical collar according to claim 9, wherein said chin support comprises a chin cushion mounted on the central bridge between the opposing wing panels.

12. An adjustable cervical collar according to claim 8, wherein said brace assembly comprises a longitudinally flexible wrap-around neck shell.

13. An adjustable cervical collar according to claim 12, wherein said brace assembly further comprises longitudinally flexible wrap-around neck cushion attached to said neck shell.

14. An adjustable cervical collar according to claim 8, wherein said slide lock further comprises a retention insert adapted to snap-fit within a shaped opening formed with said brace assembly, thereby retaining said slide lock in the gear-locked position.

15. An adjustable cervical collar according to claim 8, and comprising a numerical height indicator displaying a selected height level of said adjustable chin support relative to said brace assembly.

* * * * *